(12) United States Patent
Robinson et al.

(10) Patent No.: US 7,104,834 B2
(45) Date of Patent: Sep. 12, 2006

(54) SYSTEM AND METHOD FOR CONNECTING AN ELECTROSURGICAL INSTRUMENT TO A GENERATOR

(75) Inventors: William Robinson, Boulder, CO (US); Joe D. Sartor, Longmont, CO (US); Gene H. Arts, Berthoud, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 10/770,981

(22) Filed: Feb. 3, 2004

(65) Prior Publication Data

US 2004/0229496 A1    Nov. 18, 2004

Related U.S. Application Data

(60) Provisional application No. 60/448,521, filed on Feb. 20, 2003.

(51) Int. Cl.
*H01R 12/00* (2006.01)

(52) U.S. Cl. .......................................... 439/495; 439/77

(58) Field of Classification Search .................. 439/67, 439/77 I, 492, 495, 496, 656, 790, 863
See application file for complete search history.

(56) References Cited

U.S. PATENT DOCUMENTS

| | | | |
|---|---|---|---|
| 5,157,603 A | | 10/1992 | Scheller et al. |
| 5,295,857 A | * | 3/1994 | Toly ............................ 439/395 |
| 5,342,356 A | | 8/1994 | Ellman et al. |
| 5,396,062 A | | 3/1995 | Eisentraut et al. |
| 5,400,267 A | | 3/1995 | Denen et al. |
| 5,413,573 A | | 5/1995 | Koivukangas |
| 5,434,398 A | | 7/1995 | Goldberg |
| 5,511,993 A | * | 4/1996 | Yamada et al. ............. 439/610 |
| 5,605,150 A | | 2/1997 | Radons |
| 5,625,370 A | | 4/1997 | D'Hont |
| 5,651,780 A | | 7/1997 | Jackson et al. |
| 5,660,567 A | | 8/1997 | Nierlich |
| 5,664,953 A | * | 9/1997 | Reylek ........................ 439/111 |
| 5,860,832 A | * | 1/1999 | Wayt et al. .................. 439/465 |
| 5,944,553 A | * | 8/1999 | Yasui et al. .................. 439/495 |
| 5,959,253 A | * | 9/1999 | Shinchi ..................... 174/88 R |
| 6,068,627 A | | 5/2000 | Orszulak et al. |
| 6,232,556 B1 | * | 5/2001 | Daugherty et al. ....... 174/88 R |
| 6,402,743 B1 | | 6/2002 | Orszulak et al. |

(Continued)

FOREIGN PATENT DOCUMENTS

WO   WO 9608794   3/1996

OTHER PUBLICATIONS

Sonic Connections: "Flexible Circuit PTF and FCC Terminations".

(Continued)

*Primary Examiner*—Thanh-Tam Le

(57) ABSTRACT

The present disclosure relates to a connector for electromechanically connecting an electrosurgical cable to a flexible circuit board of a surgical instrument. The connector includes a fixed portion having a cavity defined therein which includes a wire guide block. A series of wire slots are defined within the wire guide block wherein each wire slot is dimensioned to receive a respective conductive wire disposed within the electrosurgical cable. The connector also includes a cap portion designed for selective, friction-fit engagement with the cavity of the fixed portion. The cap portion includes a series of detents which define a corresponding series of slots therebetween for wedging the conductive wires of the cable against a series of corresponding terminal contacts disposed on the flexible circuit board.

18 Claims, 4 Drawing Sheets

U.S. PATENT DOCUMENTS

| | | | |
|---|---|---|---|
| 6,422,896 B1 * | 7/2002 | Aoki et al. | 439/499 |
| 6,454,594 B1 * | 9/2002 | Sawayanagi | 439/467 |
| 6,653,569 B1 * | 11/2003 | Sung | 174/88 R |
| 6,685,701 B1 | 2/2004 | Orszulak et al. | |
| 6,843,682 B1 * | 1/2005 | Matsuda et al. | 439/596 |

OTHER PUBLICATIONS

Sonic Connections: "Sonicrimp Process".
Sonic Connections: "Ulstrasonic Crimping Technology for Precision Circuit Termination".
Sonic Connections: "Printed Circuit Board Terminations".
Sonic Connections: "Wire and Cable Terminations".

* cited by examiner

SYSTEM AND METHOD FOR CONNECTING AN ELECTROSURGICAL INSTRUMENT TO A GENERATOR

CROSS REFERENCE TO RELATED APPLICATION:

This application claims the benefit of priority to U.S. Provisional Application Ser. No. 60/448,521 filed on Feb. 20, 2003 by Robinson et al. the entire contents of which are incorporated by reference herein.

BACKGROUND

The present disclosure relates to an electrosurgical instrument and more particularly, the present disclosure relates to a system and method for mechanically and electrically connecting a flexible circuit board of an electrosurgical instrument to a generator. The invention also includes a manufacturing method for simplifying electrosurgical connections from the instrument to the generator.

TECHNICAL FIELD

Electrosurgical instruments are employed by surgeons to perform a variety of endoscopic or open surgical procedures for treating tissue including: cutting, coagulating, cauterizing, desiccating, sealing, and fusing. High frequency electrical power, typically radio frequency (RF) power or energy, is produced by an electrosurgical generator and applied to the tissue by the electrosurgical instrument. The electrosurgical instrument is operated and manipulated by the surgeon to perform the desired electrosurgical procedure.

It is advantageous to provide an electrosurgical instrument which is light, compact and easy to operate and maneuver in the surgical field. Therefore it is desirable to design an electrosurgical instrument having light weight and compact electrical components that are integrated within the electrosurgical instrument in an efficient manner while occupying as little space as possible. Flexible circuit boards configured to serve as interconnects and/or an assembly medium for analog and digital devices are good design alternatives for electrosurgical instruments. Flexible circuit boards also provide critical savings in weight and space consumption (i.e., more flexibility for fitting into compact and irregularly shaped places) which enable designers to design more compact and aesthetically pleasing instruments. Further, flexible circuit boards have been utilized in the past to reduce the number of mechanical connectors, facilitate wiring and possible increase the overall signal quality, circuit density, impedance control, operating temperature range and overall reliability of the circuit, thus maximizing efficiency in both cost and performance.

The connection between the electrosurgical generator and the electrosurgical instrument is typically removable, such that a first electrosurgical instrument configured for performing a first type of surgical procedure may be disconnected from the generator and a second electrosurgical instrument configured for performing a second type of surgical procedure may be connected. It is advantageous to provide the electrosurgical instrument with a connector which provides a reliable and easily removable connection to the electrosurgical generator, and in addition, provides a reliable and easily removable connection between electrical components of the instrument and the generator.

By and large, most, flexible circuit boards are integrated into electronic systems in a relatively time consuming and permanent manner (i.e., permanent connections) such as: zero insertion force (ZIF), soldering, pressure contact, stiffening, and piercing methods. In addition, some termination methods, e.g., piercing, utilize only a small fraction of the available conductor surface area for making electrical contact, i.e., an area defined by a circumference of a conductor piercing through an opening in a conductive trace on the flexible circuit board and the depth of the conductive trace. As can be appreciated, having a small contact area may reduce the overall reliability of the connection both during assembly and during repeated use. Thus, a need exists to develop a removable mechanical connector for establishing a quick, reliable and selectively removable electrical connection between a flexible circuit board of an electrosurgical instrument and a generator, where the contact surface between conductors is maximized to facilitate manufacturing reliability and repeated reliability during use.

SUMMARY

The present disclosure relates to a connector for electromechanically connecting an electrosurgical cable to a flexible circuit board of a surgical instrument. The conneceter includes a fixed portion including a cavity defined therein, the fixed portion including a wire guide block having a series of wire slots defined therein, each of the wire slots being dimensioned to receive a respective conductive wire disposed within the electrosurgical cable; and a cap portion designed for selective, friction-fit engagement with the cavity of the fixed portion, the cap portion including a series of detents which define a corresponding series of slots therebetween for wedging the conductive wires of the cable against a series of corresponding terminal contacts disposed on the flexible circuit board.

In another embodiment of the present invention, a method is provided for connecting a flexible circuit board of a surgical instrument to a plurality of conducting wires from an electrosurgical cable. The method includes the steps of providing a fixed portion disposed within the electrosurgical instrument, the fixed portion including a cavity defined therein, the cavity including a wire guide block having a plurality of slots defined therein for retaining the corresponding plurality of conductive wires therein; providing a cap portion being dimensioned for selective engagement within the cavity of the fixed portion, the cap portion including a plurality of detents depending therefrom which define a plurality of wire slots thereto between dimensioned to receive the plurality of conductive wire therein; positioning the plurality of conductive wires within the corresponding slots of the wire guide block such that each of the conductive wires traverses the cavity and is generally aligned in vertical registry with a corresponding terminal of the flexible circuit board; aligning the cap portion for engagement with the fixed portion such that each one of the plurality of conductive wires is aligned for reception within a corresponding wire slot of the cap portion; and inserting the cap portion within the cavity such that each of the conductive wires is wedged into electrical communication with a corresponding electrical contact of the flexible circuit board.

BRIEF DESCRIPTION OF THE DRAWINGS

Various embodiments of the subject instrument are described herein with reference to the drawings wherein.

DETAILED DESCRIPTION

Figure 1:
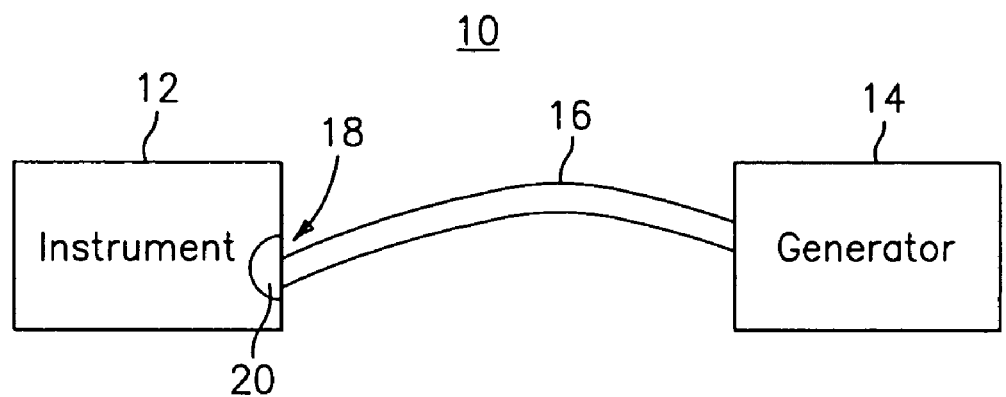
FIG. 1 is a schematic diagram of a connection between an electrosurgical instrument and an electrosurgical generator according to the present invention.

Reference should be made to the drawings where like reference numerals refer to similar elements throughout the various figures. With reference to FIG. 1, a connection is shown between components of an electrosurgical system, where the electrosurgical system is designated generally by reference numeral 10. The electrosurgical system 10 includes an electrosurgical instrument 12 connected to an electrosurgical generator 14 by a cable 16. The cable 16 connects to the electrosurgical instrument 12 at a distal end 18 via connector 20. Preferably, the electrosurgical instrument 12 is configured for performing at least one of a variety of surgical procedures on tissue such as: cutting, coagulating, cauterizating, desiccating, sealing, and fusing. It is envisioned that the instrument may be designed for either open surgery or endoscopic surgery. The term "electrosurgical energy" refers to any type of electrical energy which may be utilized for medical procedures.

Cable 16 includes a plurality of electrically conductive wires 30a, 30b, 30c which are, electrically insulated from one another (e.g., encased in an insulating covering 32). The plurality of wires 30a–30c may be further encased in an insulating covering 31. The electrosurgical generator 14 supplies electrosurgical energy to the electrosurgical instrument typically in a high frequency range (e.g., a radio frequency range) which is applied to the patient's tissue via the electrosurgical instrument 12 for facilitating the surgical procedure being performed.

Figure 2:
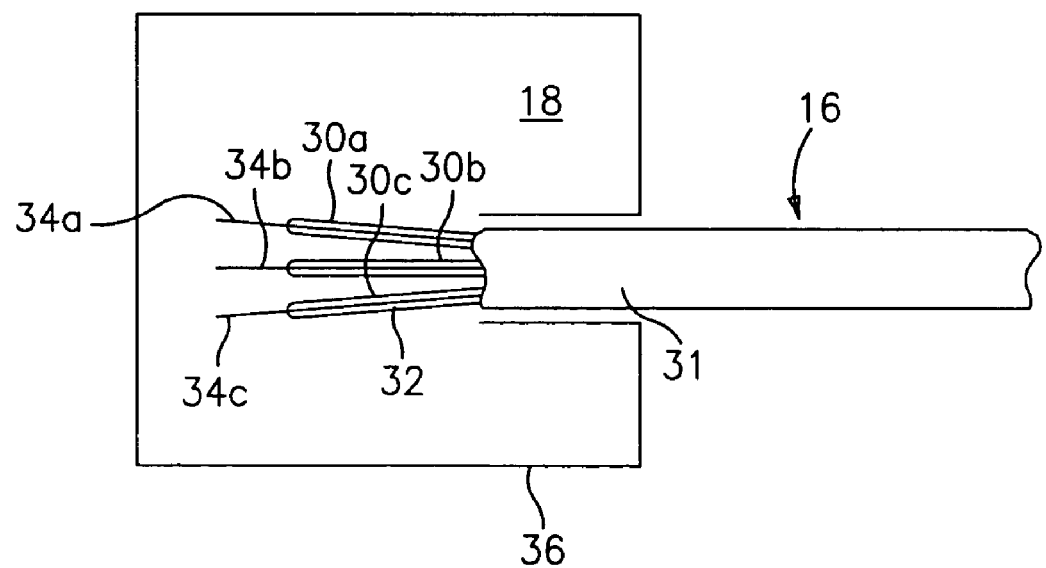
FIG. 2 is a schematic diagram of an end portion of an electrosurgical cable which connects to the electrosurgical instrument of FIG. 1.

With reference to FIG. 2, the distal end 18 of the cable 16 is shown in greater detail. As mentioned above, the plurality of wires 30a–30c are collectively insulated by a first insulation covering 31 and individually insulated by a second insulating covering 32. At a distal most end of the cable 16, the first insulating covering 31 is stripped to expose the wires 30a–30c and the second insulative coating 32 is stripped to further expose the conductive contacts 34a, 34b, 34c of each respective wire. A removable insulating cap 36 may be provided for protecting the conductive contacts 34a–34c when the cable 16 is not connected to the electrosurgical instrument 12. Preferably, the plurality of wires 30a–30c are formed of a resilient material.

Figure 3A:
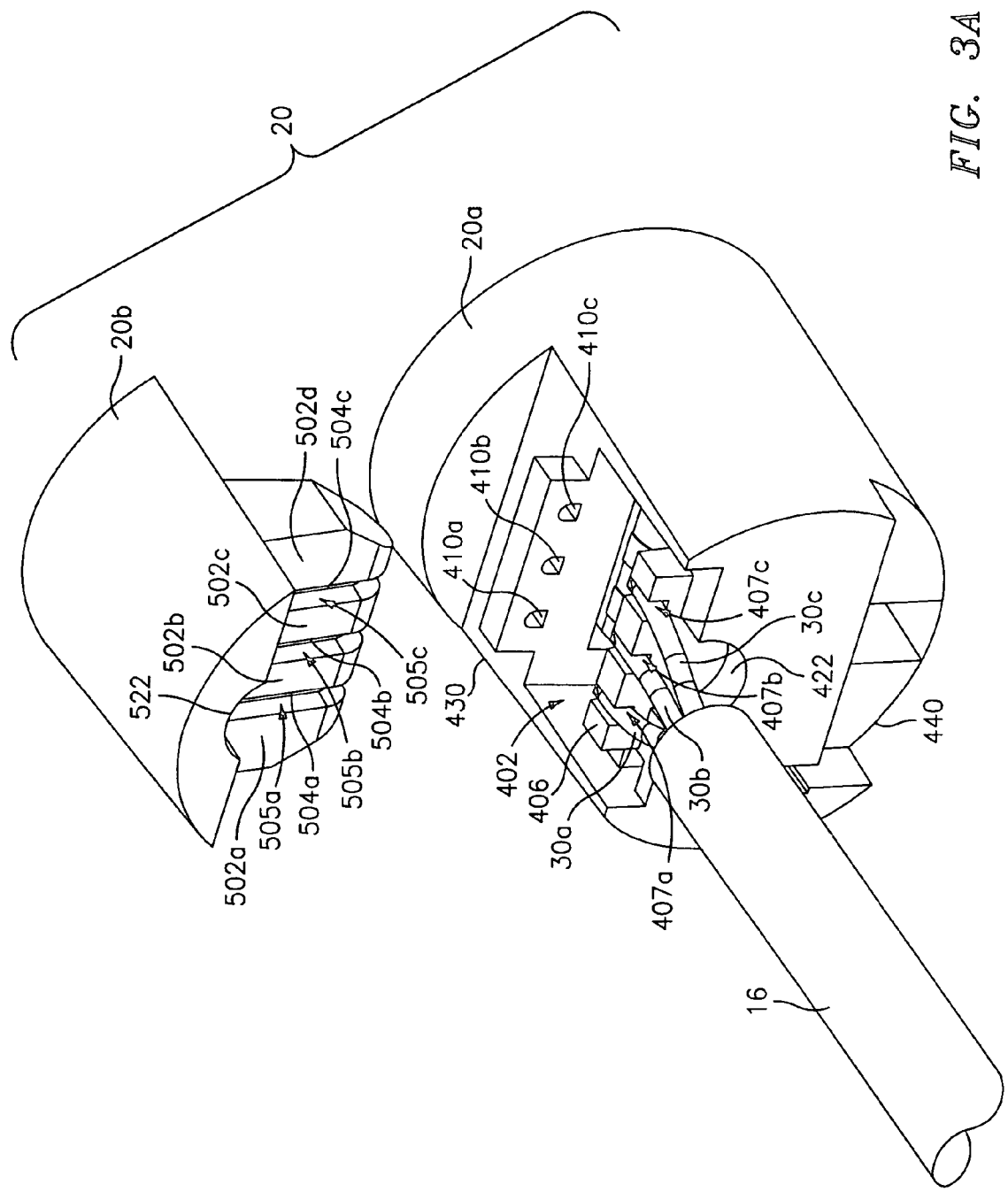
FIG. 3A is a top, first perspective view of a quick connector for use with a flexible circuit board in accordance with one embodiment of the present invention.
Figure 3B:
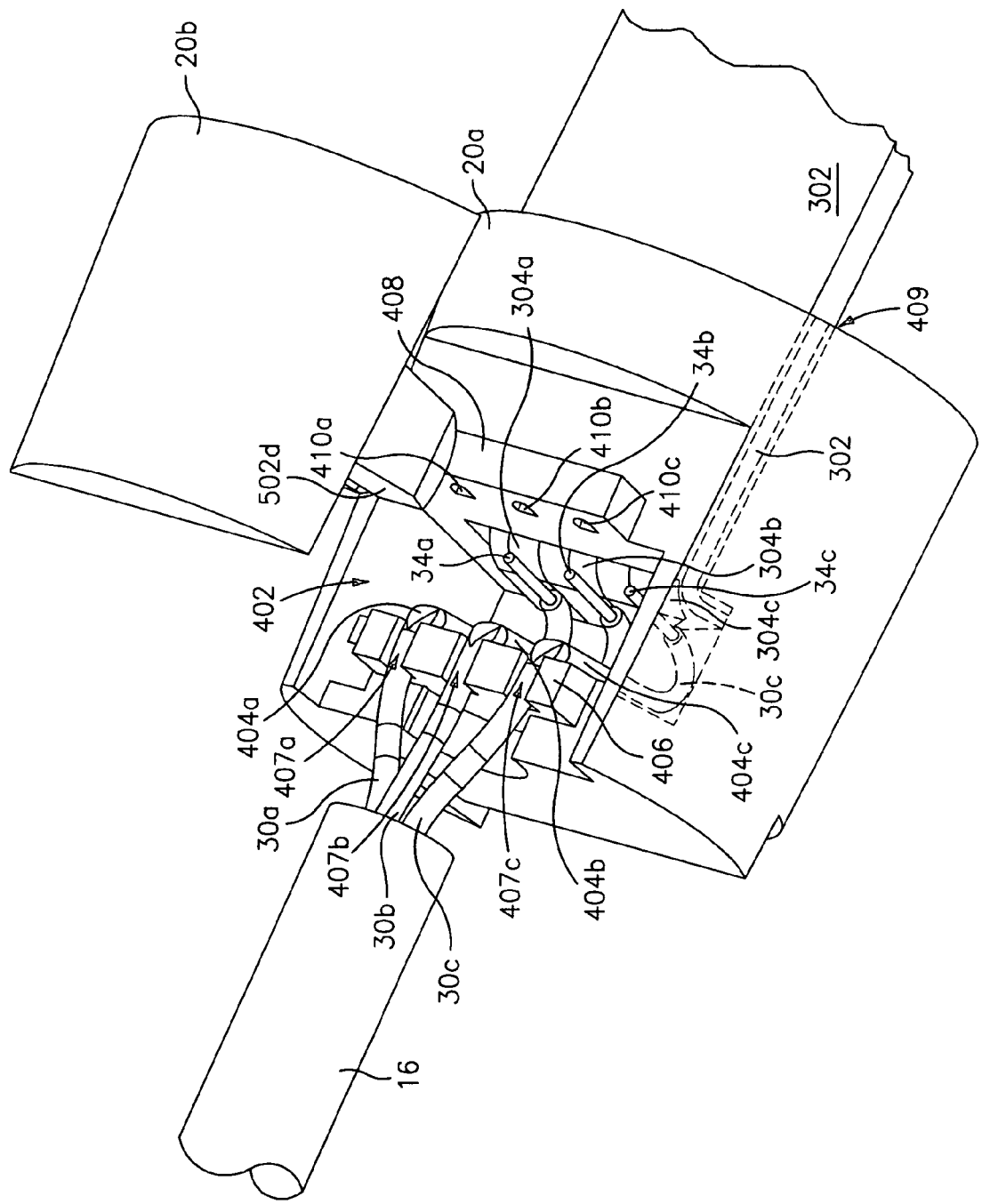
FIG. 3B is a top, second perspective view of the connector of FIG. 3A.
Figure 4:
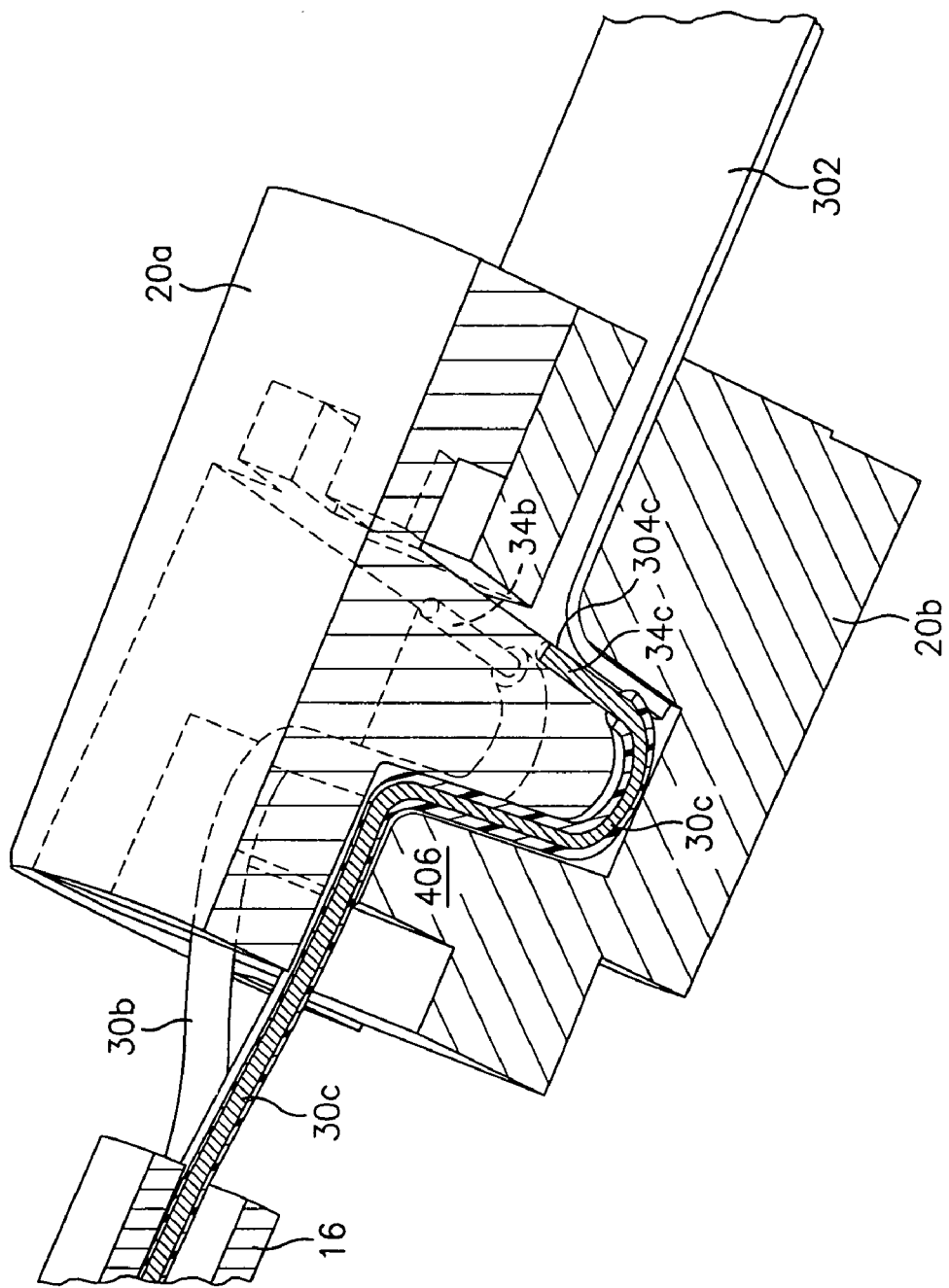
FIG. 4 is a side view of the connector of FIGS. 3A and 3B shown in a closed position connecting the end portion of the cable of FIG. 2 to the flexible circuit board of the electrosurgical instrument.

With reference to FIG. 3A, 3B and 4, quick connector 20 is shown prior to electromechanical connection to cable 16 (FIGS. 3A and 3B) and after electromechanical connection to cable 16. More particularly, the electrosurgical instrument 12 includes a flexible circuit board 302 (FCB 302) having a plurality of electrical contacts 304a, 304b and 304c (also referred to as traces, terminations or termination traces) for ultimate connection to the cable 16 via connector 20. Preferably, the connector 20 is formed of a nonconductive material and includes a fixed portion 20a and a cap portion 20b. The fixed portion 20a is embedded within a cavity (not shown) disposed in the electrosurgical instrument 12, and includes top and bottom surfaces 430 and 440, respectively. Top surface 430 includes a cavity or notch 402 disposed therein which is dimensioned to receive cable 16 and wires 30 which will be will be discussed in more detail below. Bottom surface 440 is preferably dimensioned to engage within a corresponding cavity (not shown) in instrument 12. More particularly, bottom surface 440 may include one or more mechanical interfaces which engage (e.g., snap fit, press fit, etc.) a corresponding number of mechanical interfaces disposed within the cavity of instrument 12. As can be appreciated this facilitates the manufacturing process.

As best seen in FIGS. 3A and 3B cap portion 20b is dimensioned to engage the fixed portion 20a. More particularly, cap portion 20b includes a top portion 520 having a series of mechanical interfaces 502 (e.g., detents) which engage a corresponding series of mechanical interlocks or guides 404a–404c (see FIG. 3B) disposed within cavity 402. Alternatively, it is envisioned that the wires 30a–30c may simply be held in place by virtue of the compressive forces and corresponding abutting surfaces associated with mounting cap portion 20a and 20b. Cap portion 20b also includes a series of electrical connectors 504a–504d disposed between adjacent mechanical interlocks 502 which are designed to contact the conductive contacts 34a–34c when cap portion 20b and fixed portion 20a are engaged (FIG. 4). This provides electrical continuity across the connector 20 which will be explained in more detail below.

Fixed portion 20 may be provided with cut away portion 422, and/or top portion 520 may be provided with cut away portion 522 for allowing movement or slippage of the wires 30 and/or cable 16 at a proximal portion of the distal end 18 of the wires 30, such as when the cable 16 is pulled or pushed axially, twisted or bent, while transmittal of the motion to the conductive contacts 34a–34c is prevented, thus providing stress relief. As can be appreciated, the process of forming the wires or soldering the wires to 20b creates undesirable stresses on the wires and provides little tolerance for slippage or stresses associated with assembly. It is believed that by providing a snap-fit locking interface between the wires 30a–30c and the top and bottom cap portions 20a and 20b, respectively, the various stresses associated with assembly have little or no effect to the ultimate electrical connection(s).

Fixed portion 20a also includes a wire guide block 406 which is designed to separate and align the wires 30a–30c and respective conductive contacts 34a–34c within the fixed portion 20a during assembly for subsequent engagement with the electrical connectors 504 of the cap portion 20b. More particularly, the wire guide block 406 includes a series of slots 407a, 407b and 407c disposed therein which are each dimensioned to receive a wire 30a, 30b and 30c, respectively. The slots 407a–407c may alternatively be an opening, such as an aperature or enclosed slot.

The wires 30a–30c are then fed through clamps 404 which serve a dual purpose: 1) initially retain the wires 30a–30c within fixed portion 20a; and 2) are dimensioned to mechanically engage and secure cap portion 20b with fixed portion 20a and further secure the conductive contacts 34a–34c upon engagement of the cap portion 20b. The cap portion 20b snaps into an engaged position with fixed portion 20a providing a quick electromechanical connection. Alternatively, cap portion 20b may permanently engage fixed portion 20a. It is envisioned that clamps 404 may be integrally associated with the wire guide block 406 or may be secured thereto in a separate manufacturing step.

As mentioned above, the cap portion 20b includes a series of detents 502a, 502b, 502c and 502d which extend downwardly from the top portion 520 in a finger-like fashion to define a series of slots or formed surfaces 505a, 505b and 505c therebetween. Each formed surface 505a–505c engages a corresponding clamps 404a–404c disposed within fixed portion 20a. The engagement of clamps 404a–404c and the formed surfaces 505a–505c secure the cap portion 20b to the fixed portion 20a.

Preferably, the detents 502a–502d are formed from a generally flexible material and the number of formed surfaces 505a–505c is at least equal to, and preferably the same as, the number of wires 30a–30c that are to be electrically connected to the FCB 302. Each formed surface 505a–505c may be provided with retaining features (not shown) for further retaining wires 30a–30c received therein to prevent the wires 30a–30c from slipping in a proximal or distal direction during use. As mentioned above, each formed surface 505a–505c may include a conductive element 504a, 504b, 504c for enhancing electric reliability during assembly. In other words, each of conductive elements 504a–504c may act as an electrical bridge between a respective conductive contact 34a–34c and the contacts 304a–304c of the FCB 302. Alternatively, the detents 502a–502d may be fabricated of a nonconductive material for preventing conduction between the conductive contacts 34a–34c when positioned within formed surfaces 505a–505c.

Prior to engaging the removable cap portion 20b with the fixed portion 20a, the distal end 18 of the cable 16 positioned within the fixed portion 20a (or possibly the cap portion 20b) so that each conductive contact 34a–34c is positioned with a respective slot 407a–407c in the wire guide block 406. Once the conductive contacts are properly positioned in fixed portion 20a and secured by clamps 404, the engagement of the cap portion 20b abuts the conductive contacts 34a–34c against the corresponding electrical contacts 304a–304c of the FCB 302 for establishing, retaining and maximizing electrical contact between the conductive contacts 34a–34c and the corresponding contacts 304a–304c. The cap portion 20b also maintains the conductive contacts 34a–34c in a fixed position even when the cable 16 is moved during surgical conditions.

Fixed portion 20a also includes a board slot 409 defined therein for receiving the FCB 302. It is envisioned that FCB 302 may be affixed to the fixed portion 20a by other means such as an adhesive or other mechanical connection. More particularly, during assembly, the FCB 302 is fed through slot 409 such that the FCB 302 slightly projects beyond a rear face 411 of the notch 402. When the conductive contacts 34a–34c are initially positioned within the fixed portion 20a (as explained in more detail below) and the FCB 302 is positioned within slot 409, the engagement of the cap portion 20b wedges the conductive contacts 34a–34c against the respective electrical contact 304a–304c of the FCB 302. It is envisioned that during engagement of the cap portion 20b both the conductive contacts 304a–304c and the FCB 302 move downwardly in the direction "Y" until the cap portion 20b "snaps" on wedges into secure engagement with the fixed portion 20a. it is envisioned that connecting the FCB 302 and the conductive contacts 34a–34c in this fashion will facilitate reliable engagement during assembly.

The FCB 302 preferably includes an array of conductors bonded to a thin dielectric film, configured as a single layer, single-sided, double-sided, multilayer or rigid-flex circuit board, or a combination thereof. In a single-sided configuration the FCB 302 includes a single conductive layer. In a double sided configuration the FCB 302 includes two conductive layers that are usually accessible from both sides. In a multilayer configuration the FCB 302 includes more than two layers, where Interconnection between layers is usually by means of plated-through holes. In a rigid-flex configuration the FCB 302 combines flexible circuitry with rigid PC board technology. It is also envisioned that the FCB 302 may incorporate surface mount technology (SMT) providing a strain-free bonding site for an SMT device. Contacts 304a–304c are provided for making electrical contact with other electrical components, such as the wires 30a–30c of cable 16.

A second guide portion 408 is preferably provided, which includes a series with alignment openings 410a, 410b and 410c defined therein which are aligned in general horizontal registry within slots 407a, 407b and 407c. The second guide portion 408 is used to initially position the conductive contacts 34a–34c in proper alignment within the fixed portion 20a prior to engagement of the cap portion 20b, i.e., each conductive contact 34a–34c is inserted through a respective alignment opening 410a, 410b, 410c. As mentioned above, upon engagement of cap portion 20b each conductive contact 34a–34c is wedged into electrical contact with a corresponding contact 304a–304c of the FCB 302. Preferably the slots 407a–407c and clamps 404a–404c initially retain each wire 30a–30c in its initial position prior to engagement of cap portion 20b while the openings 410a–410c of the second guide portion 408 maintain the conductive contact 34a–34c in proper alignment for ultimate contact with the FCB 302. Additional retaining means (not shown) may be provided within the cavity 402 for assisting the positioning and/or the retaining of the wires 30a–30c either prior to or after engagement of the cap portion 20b, e.g., a series of flexible or retractable lips provided on the inner walls or on the bottom surface of the cavity 402.

Preferably, detents 502a–502d include one or more tapered portions to facilitate assembly and to assure a tight, friction fit of the cap portion 20b within the fixed portion 20a. For example, as shown in FIGS. 3A and 3B, the side walls 532 of detents 502a and 502d are inwardly and downwardly tapered to guide and align the cap portion 20b into the cavity 402 of the fixed portion 20a. Detents 502a–502d may also be formed of a flexible material, such that the width of the formed surfaces 505a–505c is reduced (i.e., "squeezed") when the cap portion 20b is inserted into the cavity 402. It is further contemplated that inner walls of the cavity 402 may be tapered and/or provided with one or more grooves (not shown) for guiding the cap portion 20b into place during assembly.

As the wires 30a–30c engage respective slots 504a–504c, the slots 504a–504c align and orient the conductive contacts 34a–34c of the respective wires 30a–30c and guide the contacts 34a–34c into proper termination locations on the FCB 302. The wires 30a–30c are retained in position so that the conductive contacts 34a–34c of each wire 30a–30c is pressed against a corresponding electrical contact 304a–304c, respectively, of the FCB 302 in surface-to-surface contact along a length thereof. It is envisioned that communication of clamps 404a–404c and the mechanical friction engagement of the conductive contacts 34a–34c against the terminal contacts 304a–304c of the FCB 302 cooperate to prevent slippage of the wires 30a–30c during use. Thus, during assembly engagement of the fixed portion 20a and cap portion 20b creates and maintains a reliable and secure electrical contact for allowing a flow of current between wires 30a–30c and the electrical contacts 304a–304c of the FCB 302 without requiring soldering (or additional electrical components or connectors). Furthermore, the surface-to-surface contact between the conductive contacts 34a–34c of each wire 30a–30c and the corresponding electrical contacts 304a–304c of the FCB 302 results in a relatively large contact surface area and improved conductivity.

It is envisioned that the cap portion 20b may be configured for selective removal from the body portion 20a. Cap portion 20b may also be designed to initially receive and/or selectively retain the conductive contacts 34a–34c of the wires 30a–30c in a correct orientation prior to engagement of the cap portion 20b and fixed portion 20a which, as can be appreciated, allows for multiple engagements and disengagements of the cap portion 20b with the fixed body portion 20a, thus functioning as a quick disconnect. It is further envisioned that during insertion of the cap portion 20b within the cavity 402, the cap portion 20b asserts pressure on the FCB 302, causing a portion of the FCB 302 into electrical contact with the conductive wires 30a–30c.

Although this disclosure has been described with respect to preferred embodiments, it will be readily apparent to those having ordinary skill in the art to which it appertains that changes and modifications may be made thereto without departing from the spirit or scope of the disclosure. For example it is envisioned that either the cap portion 20b or the fixed portion 20a may include one or plurality of LED (light emitting diodes) or other visual indicators which provide visual feedback regarding the electrical integrity of each electrical connection between the conductive wires 30a–30c and the terminal contacts 304a–304c. Moreover, although three (3) conductive wires are shown in the various figures, it is contemplated that any number of conductive wires 30a–30x may be employed with a corresponding number of terminal contacts 304-304x (and other internal components of the cap portion 20b and fixed portion 20a, e.g., detents, wire guide slots, alignment openings, clamps, etc.).

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A connector for electromechanically connecting an electrosurgical cable to a flexible circuit board of a surgical instrument, said connector comprising:
   a fixed portion including a cavity defined therein, said fixed portion including a wire guide block having a series of wire slots defined therein, each of said wire slots being dimensioned to receive a respective conductive wire disposed within the electrosurgical cable, wherein said respective conductive wire is insulated by an insulation covering; and
   a cap portion designed for selective, friction-fit engagement with said cavity of said fixed portion, said cap portion including a series of detents which define a corresponding series of slots therebetween which wedge exposed conductive contacts of said conductive wires of the cable against a series of corresponding terminal contacts disposed on the flexible circuit board to provide electrical continuity therebetween, wherein the cavity is adjacent the plurality of slots.

2. The connector in accordance with claim 1, wherein said cap portion includes a series of conductive elements which are dimensioned to insure electrical continuity between said conductive wires of the electrosurgical cable.

3. The connector in accordance with claim 1, wherein said fixed portion includes a board slot which guides the flexible circuit board through the connector into the cavity for ultimate connection to said wires of the cable.

4. The connector in accordance with claim 1, wherein said fixed portion includes at least one clamp for retaining said wires in substantially secure position within said fixed portion.

5. The connector in accordance with claim 1, wherein said fixed portion includes a series of alignment openings defined therein for temporarily aligning each of said wires prior to engagement of the cap portion, each of said alignment openings being in substantial vertical registration with a respective terminal contact of the flexible circuit board.

6. The connector in accordance with claim 5, wherein upon engagement of said cap portion with said fixed portion, each of said slots between each of said detents engulfs a respective wire and wedges said wire into contact with a corresponding terminal contact in the flexible circuit board.

7. The connector in accordance with claim 1, wherein said detents of said cap portion are made from a generally resilient material.

8. The connector in accordance with claim 1, wherein at least one of said detents of said cap portion is tapered.

9. The connector in accordance with claim 1, wherein said fixed portion includes a series of mechanically interfacing surfaces which mate with a corresponding series of mechanically interfacing surfaces disposed within each cap portion to secure said cap portion to said fixed portion.

10. A connector for connecting a flexible circuit board to a plurality of conductive wires for connection to an electrosurgical generator, the connector comprising:
    a fixed portion having a cavity defined therein, said cavity receiving a terminal end of the flexible circuit board to expose a plurality of electrical contacts within the cavity;
    a cap portion having a plurality of detents projecting therefrom which define slots for receiving the corresponding plurality of conductive wires therein, wherein each of the plurality of conductive wires is insulated by an insulation covering, and wherein the cavity is adjacent the plurality of slots;
    wherein insertion of said cap portion within said cavity of said fixed portion initially aligns said each of the plurality of conductive wires within said slots of said cap portion in registry with said plurality of electrical contacts and subsequently wedges an exposed of said each conductive wire to establish electrical contact between said each conductive wire and a corresponding electrical contact of the flexible circuit board.

11. The connector in accordance with claim 10, wherein during insertion of said cap portion within the cavity, said cap portion asserts pressure on the flexible circuit board causing a portion of the flexible circuit board to flex into electrical contact with said conductive wires.

12. The connector in accordance with claim 10, wherein the fixed portion is provided with a wire guide block having a first plurality of openings defined therein, each of said plurality of openings being capable of receiving a respective conductive wire therein.

13. The connector in accordance with claim 12, wherein the fixed portion further includes a second plurality of openings, each of said second plurality of openings being capable of receiving a respective conductive wire therein, said first and second plurality of openings being located across said cavity.

14. The connector in accordance with claim 13, wherein said first and second plurality of openings cooperate to align said conductive wires in substantial vertical registration with said electrical contacts of said flexible circuit board.

15. The connector in accordance with claim 14, wherein upon insertion of said cap portion into said fixed portion each respective conductive wire is wedged against a corresponding electrical contact of said flexible circuit board.

16. A method for connecting a flexible circuit board of a surgical instrument to a plurality of conducting wires from an electrosurgical cable, said method comprising the steps of:
   providing a fixed portion disposed within the electrosurgical instrument, said fixed portion including a cavity defined therein, said cavity including a wire guide block having a plurality of slots defined therein for retaining said corresponding plurality of conductive wires therein, wherein the cavity is adjacent the plurality of slots;
   providing a cap portion being dimensioned for selective engagement within said cavity of said fixed portion, said cap portion including a plurality of detents depending therefrom which define a plurality of wire slots there between dimensioned to receive said plurality of conductive wires therein;
   positioning said plurality of conductive wires within said corresponding slots of said wire guide block such that each of said conductive wires traverses said cavity and is generally aligned in vertical registry with a corresponding terminal of said flexible circuit board, and wherein said each conductive wire is insulated by an insulation covering;
   aligning said cap portion with said fixed portion such that said each conductive wire is aligned for reception within a corresponding wire slot of said cap portion; and
   inserting said cap portion within said cavity such that exposed conductive contact of said each conductive wire is wedged into electrical communication with a corresponding electrical contact of said flexible circuit board.

17. The connector in accordance with claim 16, wherein after said providing steps, the method further includes the step of:
   positioning said flexible circuit board within said cavity to expose a plurality of electrical contacts.

18. The connector in accordance with claim 16, wherein after said positioning steps, the method further includes the step of:
   aligning each of said conductive wires within a corresponding alignment opening defined in said fixed portion to align said conductive wires in vertical registration with said electrical contacts of said flexible circuit board.

* * * * *